(12) United States Patent
Heim et al.

(10) Patent No.: US 9,731,727 B2
(45) Date of Patent: Aug. 15, 2017

(54) METHOD AND DEVICE FOR DETECTING THE ALERTNESS OF A VEHICLE DRIVER

(71) Applicant: Robert Bosch GmbH, Stuttgart (DE)

(72) Inventors: Oliver Heim, Wuerzburg (DE); Charbel Assaf, Kanagawa (JP)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/074,825

(22) Filed: Mar. 18, 2016

(65) Prior Publication Data

US 2016/0297449 A1 Oct. 13, 2016

(30) Foreign Application Priority Data

Apr. 8, 2015 (DE) .......................... 10 2015 206 200

(51) Int. Cl.
*B60W 40/09* (2012.01)
*B60W 30/08* (2012.01)
*G06K 9/00* (2006.01)

(52) U.S. Cl.
CPC ............ *B60W 40/09* (2013.01); *B60W 30/08* (2013.01); *G06K 9/00845* (2013.01); *B60W 2420/42* (2013.01); *B60W 2540/30* (2013.01); *B60W 2710/30* (2013.01); *B60W 2900/00* (2013.01)

(58) Field of Classification Search
CPC combination set(s) only.
See application file for complete search history.

(56) References Cited

U.S. PATENT DOCUMENTS

| | | | |
|---|---|---|---|
| 8,965,037 B2* | 2/2015 | Levin ..................... | A61B 3/113 382/100 |
| 2011/0169625 A1* | 7/2011 | James .................... | B60Q 9/008 340/439 |
| 2012/0154441 A1* | 6/2012 | Kim .................. | G06K 9/00832 345/633 |
| 2014/0321705 A1* | 10/2014 | BenHimane ......... | G06K 9/6211 382/103 |

* cited by examiner

*Primary Examiner* — Thomas G Black
*Assistant Examiner* — Ana Thomas
(74) *Attorney, Agent, or Firm* — Norton Rose Fulbright US LLP; Gerard Messina

(57) ABSTRACT

A method for detecting the alertness of a vehicle driver includes the detection of a potentially dangerous situation by a system of the vehicle; the estimation of a visual observation field of the vehicle driver; and the detection of the alertness of the vehicle driver by comparing an orientation or a position of the potentially dangerous situation to the visual observation field of the vehicle driver.

13 Claims, 2 Drawing Sheets

METHOD AND DEVICE FOR DETECTING THE ALERTNESS OF A VEHICLE DRIVER

CROSS REFERENCE

The present application claims the benefit under 35 U.S.C. §119 of German Patent Application No. 102015206200.7 filed on Apr. 8, 2015, which is expressly incorporated herein by reference.

FIELD

The present invention relates to a method and a device for detecting the alertness of a vehicle driver, in particular a vehicle driver wearing a portable sensor unit on the head.

BACKGROUND INFORMATION

Active driver assistance systems or safety systems (PSS, Predictive Safety System), which autonomously brake vehicles in dangerous situations with the aid of radar and/or video sensor systems, have come into widespread use. However, such systems do not know whether a potentially dangerous situation is caused by the alertness of the driver. These systems therefore always constitute a compromise between a benefit and a faulty warning. For example, the benefit may possibly have to be reduced in order to prevent premature warnings of attentive drivers. Faulty warnings, on the other hand, must be accepted, so that a timely warning can be given to a driver whose attention is wandering just then.

Such systems therefore make it necessary to collect as much information as possible with regard to the current alertness of the driver in order to point out or react to dangerous situations in a timely yet not premature manner. Current systems infer the alertness of the vehicle driver from vehicle parameters or from the driving behavior.

SUMMARY

An example method of the present invention for detecting the alertness of a vehicle driver includes, for example, the following:
Detecting a potentially dangerous situation with the aid of a system of the vehicle;
Estimating a visual observation field of the vehicle driver;
Detecting the alertness of the vehicle driver by comparing an orientation or a position of the potentially dangerous situation to the visual observation field of the vehicle driver.

The example method of the present invention has the advantage that the visual observation field is estimated or ascertained, so that information can be provided about the alertness or the direction of attention of the vehicle driver. The visual observation field, for example, is ascertainable via a portable sensor unit, which, for example, may be part of an augmented reality system or a wearable device such as smartglasses. By comparing the visual observation field with an orientation or position of a potentially dangerous situation, the alertness of the vehicle driver is able to be determined at all times in a definitive manner. This real-time determination of the vehicle driver's alertness is clearly more precise and up-to-date than current alertness measures, which merely constitute an integration of what has already happened up to that point and a derivation of the general driver alertness that follows therefrom.

The visual observation field can be estimated on the basis of a head orientation and/or a gaze direction of the vehicle driver. The use of at least one of the two criteria allows an estimation of the visual observation field, which constitutes a measure of the alertness of the vehicle driver when steering a vehicle.

A warning signal is able to be output and/or an intervention in the driving operation of the vehicle may take place if the orientation of the potentially dangerous situation and the visual observation field do not agree or deviate from one another. The passive development of the method in the sense of a warning signal alerts the vehicle driver when his or her attention is not directed to the potentially dangerous situation or when the attention is focused in another direction. The warning may be output by a system of the vehicle and/or the camera unit.

This active development of the method within the sense of an intervention intervenes in the driving operation when the attention of the vehicle driver is not directed to the potentially dangerous situation. For example, an intervention describes a braking operation or the preparation of a breaking operation and/or the activation of safety systems.

The intensity, duration, type and/or starting instant of the warning signal and/or the intervention may be a function of a degree of alertness. The degree of alertness, for example, may be defined on the basis of the comparison between an orientation or a position of the potentially dangerous situation and the visual observation field of the vehicle driver. A more pronounced difference between orientation and visual observation field may therefore indicate a lower degree of alertness, while a smaller difference between orientation and visual observation field corresponds to a higher degree of alertness. Depending on the alertness, the warning or the intervention may be output earlier or later. It is also possible to output the warning or perform the intervention in stronger or weaker terms, such as with regard to the volume of the signal tone or the intensity of a braking pressure. The warning or the intervention is thereby adaptable to the individual situation.

The visual observation field can be estimated with the aid of a sensor unit worn on the head of the vehicle driver; it can be determined based on at least one optical feature of the vehicle in a recording of a camera unit of the portable sensor unit, based on at least one indication of the cardinal direction of a device for acquiring the cardinal direction of the portable sensor unit, and/or on the basis of at least one signal from an acceleration sensor of the portable sensor unit. The recording may include an image, a video or a spectrum, such as an infrared spectrum, for instance. The optical feature might be an already existing feature of the vehicle, such as the steering wheel, the exterior rear-view mirror or other elements of the interior or exterior space of the vehicle. However, the optical features may also be specially applied markings, which are advantageously distributed across the visual field of the vehicle driver. The resolution or accuracy of the detection of the head orientation is able to be adjusted via the number and/or position of the features. The optical feature, for example, may be an infrared source such as an IR-LED, which the driver is unable to perceive and which therefore does not intrude. This may have the additional advantage that the camera unit can perceive it even in darkness. The indication of the cardinal direction or the orientation may be used as an alternative or in addition. These signals or measured values may be generated with the aid of a compass, a magnetometer or a Hall-effect sensor of the portable sensor unit, for instance. As an alternative or in addition, measured values from one or multiple acceleration sensor(s) of the portable sensor unit may be utilized, via which an inclination and/or rotation of the head can be discerned. These features are combinable with each other or may be used as features on their own. The different measured values, for example, can be used to plausibilize the situation and/or individual measured values.

The potentially dangerous situation may be indicated by the orientation or position of an object. Safety or assistance systems quite frequently operate in an object-based manner, thereby allowing the often more precise description by an object such as a vehicle or an object. Moreover, an object identification of the recording may be used for ascertaining the alertness.

An example device for detecting the alertness of a driver of a vehicle according to the present invention, which includes a system for detecting a potentially dangerous situation, is characterized in that a sensor unit is provided, which is designed to estimate a visual observation field of the vehicle driver; in that a communications module is provided for the communication with the system and the sensor unit; and in that a computer device is made available, which is designed to detect the alertness of the vehicle driver by comparing an orientation or a position of the potentially dangerous situation with the visual observation field of the vehicle driver. The portable sensor unit may be situated in an augmented reality system or a wearable computer. This system, for example, can be smartglasses or a smart contact lens. In cases of this type, a camera unit of such a system and also the imaging unit may be used to provide the vehicle driver with warnings and/or information. The same advantages and modifications apply as described above.

The computer unit may be situated in the system and/or in the sensor unit. Control units, such as a vehicle assistance control unit (DAS-ECU (Driver Assistant System-Electronic Control Unit), include computer units which are capable of carrying out such calculations in a rapid manner. A computer unit of this kind may also be installed in the camera unit, or in a system containing the camera unit, such as an augmented reality system. In addition, the computer unit may be included in a further system which communicates with the system and the camera unit.

At least one optical feature, in particular an infrared transmitter, may be provided on the vehicle for the purpose of being perceived as a reference point in a recording of the sensor unit. In an advantageous manner, the visual observation field of the vehicle driver is able to be ascertained via the optical feature and its known position on the vehicle. The optical feature can be a marking, specifically provided for this purpose, or an already existing feature, such as the steering wheel or the exterior rear-view mirror. Already existing features together with their position may be stored in a database in order to be identifiable in the recording of the camera unit via a detection routine. A vehicle driver will not notice an infrared transmitter, so that his attention will not be distracted.

The system may have at least one camera, which is set up to detect the pupillae, and thereby the gaze direction of the driver, and the computer unit is designed to superpose the gaze direction onto the visual observation field. Moreover, the use of one/multiple camera(s) in the direction of the driver's pupillae makes it possible to detect the gaze direction and to superpose it onto the head orientation. This allows greater accuracy and/or a further plausibilization.

BRIEF DESCRIPTION OF THE DRAWINGS

Exemplary embodiments of the present invention are explained in greater detail below with reference to the figures.

DETAILED DESCRIPTION OF EXAMPLE EMBODIMENTS

Figure 1:
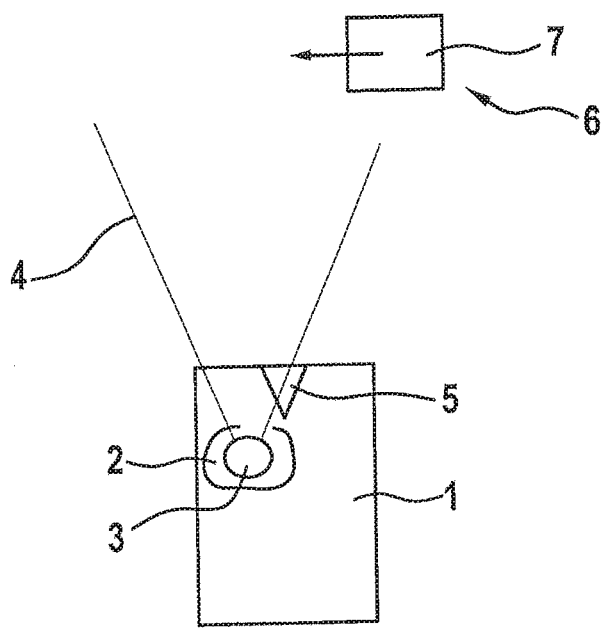
FIG. 1 shows a schematic representation of a situation featuring an alert vehicle driver.

FIG. 1 schematically shows a vehicle 1 with a vehicle driver 2 who is driving vehicle 1. For example, the vehicle can be a land-bound vehicle or a motor vehicle such as a passenger car, truck, bus, motor cycle, a rail vehicle such as a locomotive or street car, an aircraft such as a passenger aircraft, or a watercraft, such as a boat or ferry.

A head 3 of vehicle driver 2 is situated in a certain orientation, the head orientation generally corresponding to the direction of attention of vehicle driver 2. In addition or as an alternative to the head orientation, the gaze direction of vehicle driver 2 is able to be utilized for estimating a visual observation field of vehicle driver 2. While a determination of the head orientation is assumed by way of example in the following figure description, the detection or estimation of the visual observation field is encompassed as well.

To illustrate the head orientation in FIG. 1, a field of view 4 of vehicle driver 2 has been sketched. The head orientation therefore lies in the driving direction of vehicle 1. The main interest here is the head orientation of vehicle driver 2 in the movement plane of vehicle 1, i.e., in an X-Y plane. In other words, it is of interest in this case whether vehicle driver 2 gazes toward the left or right, or toward the front or back. Since the attention of a vehicle driver 2 lies predominantly in the driving direction, i.e., is usually directed toward the front, under certain circumstances it may be possible to restrict the detection of the head orientation to the Y plane, that is, a direction to the left or right in relation to the driving direction.

Head orientations in the Z plane, as well, i.e., from above to below, may be monitored here, so that it is also possible to sense the Z direction. This makes it possible to detect scenarios in which the driver or his attention is drawn to a region below or above the normal field of vision, i.e., the windshield. For example, this may be the case when the driver is busy with an operating element such as a radio, or if he gazes at the operating unit of a sliding roof. In other words, it is detectable whether the head is inclined toward below or above.

A system 5, such as a driver assistance system or a safety system, for example, is situated in vehicle 1; it monitors the environment, or at least the region lying in front of vehicle 1 in the driving direction, for potentially dangerous situations 6. A potentially dangerous situation 6 is a situation that may lead to a collision with a potentially dangerous object 7 if vehicle 1 and/or object 7 maintain(s) their current heading or their current speed. To record the environment, system 5 includes radar and/or video sensors, for example, which may be implemented as stereo or mono sensors.

In the situation shown in FIG. 1, the head orientation, and thus viewing angle 4 of motor vehicle driver 2, is aligned in such a way that he is able to notice object 7. As a result, dangerous situation 6 or dangerous object 7 lies within the attention of vehicle driver 2.

Figure 2:
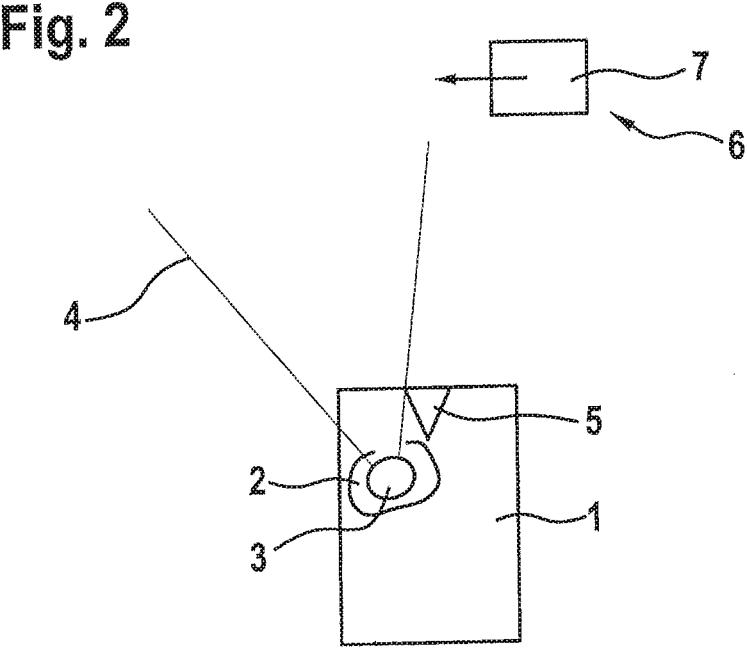
FIG. 2 shows a schematic representation of a situation featuring in inattentive vehicle driver.

FIG. 2 shows a similar situation, in which vehicle 1, driven by vehicle driver 2, and object 7 are on a collision course. System 5 has already sensed dangerous object 7. In contrast, the attention of vehicle driver 2 is not focused on object 7, as is shown from the illustrated viewing angle 4. The head orientation of vehicle driver 2 faces away from object 7 or from potentially dangerous situation 6. Without a warning to vehicle driver 2 and/or without an intervention of system 5 in the driving operation of vehicle 1, there exists a serious collision risk between vehicle 1 and object 7.

Figure 3:
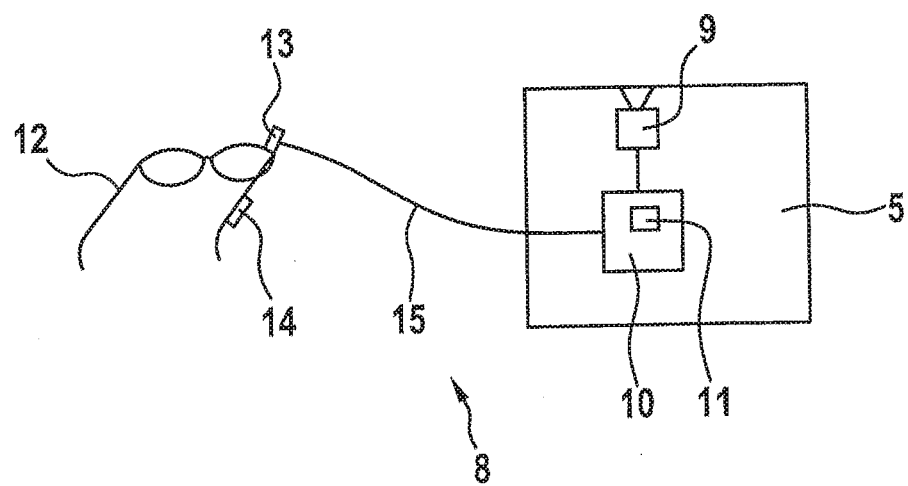
FIG. 3 shows a schematic representation of a device for alertness detection.

FIG. 3 schematically shows a device 8 according to the present invention for detecting the alertness of a vehicle driver 2. System 5 of vehicle 1 includes a camera 9, which records the space in front of vehicle 1, in particular the potentially dangerous situation 6 with object 7. The sensor values are made available to a control unit 10 of system 5. Control unit 10 includes a computer unit 11, on which the method for alertness detection is carried out at least partially.

An augmented reality system or a portable sensor unit 12, in this instance shown in the form of smartglasses by way of example, encompasses a camera unit 13, which makes recordings, such as images or video films, from the viewpoint of vehicle driver 2. In addition, augmented reality system 12 includes a computer unit 14. Portable sensor unit 12 advantageously includes additional sensors, for instance a compass or similar device, for ascertaining the cardinal direction or orientation, and/or acceleration sensors.

While a portable sensor unit is described within the context of the exemplary embodiment shown in the figures, the sensor unit may alternatively or additionally also be integrated in the vehicle.

A communications device 15 links augmented reality system 12 to system 5 or control unit 10. Communications connection 15 can be part of a vehicle bus system, such as a CAN or FlexRay. Communications connection 15 may be compatible with further cabled or wireless connection types or connection protocols, for instance Bluetooth, W-LAN, USB, etc.

Below, the way in which way the attention of vehicle driver 2 is ascertained will be described with the aid of the figures.

By monitoring the environment of vehicle 1, system 5 detects a potentially dangerous situation 6, such as the movement of object 7 into the current driving path of vehicle 1.

Subsequently or at the same time, the head orientation of vehicle driver 2 is detected with the aid of the sensors of portable sensor unit 12. For example, a recording of camera unit 12 is used and possibly supplemented by measured values of the further sensors in so doing. One or more image(s) of camera unit 13, for instance, is/are analyzed for this purpose, which may take place in computer unit 14 or computer unit 11. By comparing the recording or sections or parts of the recording with optical features of the vehicle that are known in their appearance and position, such as the steering wheel or a specially applied marking, the head orientation of vehicle driver 2 is determined.

In FIG. 1, for example, the head orientation of vehicle driver 2 is straight forward, or 0° in relation to the driving direction of vehicle 1. In FIG. 2, the head orientation of vehicle driver 2 is to the left or, in other words, it amounts to approximately −30° in relation to the travel direction of vehicle 1.

The head orientation of vehicle driver 2 is now compared to the orientation or position of potentially dangerous situation 6 or object 7. The orientation of object 7, i.e., the alignment with respect to the current driving direction, amounts to approximately 20° in FIGS. 1 and 2.

In the situation according to FIG. 1, the difference between the position and head position amounts to 20°, and in the situation according to FIG. 2, the difference between the position and head position amounts to 50°. It is now possible to define a criterion that indicates a tolerable difference. For applications that are highly safety-relevant, the criterion or the limit value may amount to 0° or close to 0°, so that sufficient alertness of vehicle driver 2 is inferred only if there is a precise agreement between position and head position. In all other cases, the criterion may be 25°, for example, so that sufficient alertness of vehicle driver 2 will be determined for the situation according to FIG. 1. Insufficient alertness of vehicle driver 2 is found for the situation according to FIG. 2.

Computer units 11 and/or 14 carrying out the alertness detection receive(s) the orientation and/or position of object 7 and optionally also further information, such as, for example, an ascertained collision time, the movement direction of object 7, etc. Based on an individual or multiple recording(s) of camera unit 13, computer unit 11 and/or 14 check(s) the gaze direction of the driver, for example by detecting certain vehicle interior features, exterior vehicle features, special optical features or features outside the vehicle, such as road markings (this may be lines in front of the vehicle, for example).

Depending on the ascertained head orientation or gaze direction of vehicle driver 2, computer unit 11 and/or 14 decide(s) whether the time has come already to give a warning to driver 2 because the driver is not gazing in the direction of dangerous object 7, for instance while he is glancing over the shoulder in connection with a lane change, as shown in FIG. 2. Or computer unit 11 and/or 14 decide(s) that the attention is sufficient to dispense with a warning at this point, as illustrated in FIG. 1. This is meant to avoid faulty warnings.

If a warning is to be output, vehicle driver 2 receives a timely warning by way of a suitable signal. This may be an optical signal, output for instance from augmented reality system 12 or a vehicle information unit. In addition, an acoustic warning signal may be provided, which is output by an audio unit of vehicle 1 and/or augmented reality system 12. Moreover, a haptic warning, such as on the steering wheel of vehicle 1, is possible.

For an active reaction of the alertness detection, an intervention in the driving operation of the vehicle is performed when the orientation and head orientation do not agree, or if their difference is excessive. In this case information pertaining to the alertness or inattentiveness of vehicle driver 2 are returned to control unit 10 provided the calculations have not been performed there. Control unit 10 then induces autonomous braking or a preliminary activation of the brakes, for instance, in an attempt to shorten the breaking distance.

What is claimed is:

1. A method for ascertaining an alertness of a vehicle driver, characterized by the steps:

detecting a potentially dangerous situation by a system of the vehicle;

detecting at least one optical feature of the vehicle as a reference point, the at least one optical feature having a known position on the vehicle;

receiving at least one image recorded by a camera unit;

estimating a visual observation field of the vehicle driver by comparing the at least one image with the position of the at least one optical feature; and detecting the alertness of the vehicle driver by comparing an orientation or a position of the potentially dangerous situation to the visual observation field of the vehicle driver.

2. The method as recited in claim 1, further comprising: outputting a warning signal if the orientation of the potentially dangerous situation and the visual observation field do not agree.

3. The method as recited in claim 2, wherein at least one of an intensity, a duration, a type, and a starting instant of the warning signal is a function of the detected alertness.

4. The method as recited in claim 1, further comprising: intervening in a driving operation of the vehicle if the orientation of the potentially dangerous situation and the visual observation field do not agree.

5. The method as recited in claim 4, wherein at least one of an intensity, a duration, a type, and a starting instance of the intervention is a function of the detected alertness.

6. The method as recited in claim 1, wherein the visual observation field is ascertained based on at least one of: i) a plurality of optical features of the vehicle in a recording of the camera unit, ii) at least an indication of a cardinal direction of a device for detecting a cardinal direction of a portable sensor unit and iii) at least one signal from an acceleration sensor of the portable sensor unit.

7. The method as recited in claim 1, wherein the potentially dangerous situation is indicated by the orientation or position of an object.

8. The method as recited in claim 1, further comprising adjusting at least one of a resolution and accuracy of the estimated visual observation field based on at least one of a number and a position of the at least one optical feature.

9. A device for alertness detection of a vehicle driver of a vehicle having a system for detecting a potentially dangerous situation, comprising:
a sensor unit designed to:
detect at least one optical feature of the vehicle as a reference point, the at least one optical feature having a known position on the vehicle;
receive at least one image recorded by a camera unit; and
estimate a visual observation field of the vehicle driver by comparing the at least one image with the position of the at least one optical feature;
a communications module for communication with the system and the sensor unit; and
a computer unit set up to detect alertness of the vehicle driver by comparing an orientation or a position of the potentially dangerous situation to the visual observation field of the vehicle driver.

10. The device as recited in claim 9, wherein the computer unit is situated in at least one of the system and in the portable sensor unit.

11. The device as recited in claim 9, wherein the at least one optical feature is an infrared transmitter.

12. The device as recited in claim 9, wherein the system has at least one camera designed to record pupillae, and thus a gaze direction, of the driver, the computer unit being designed to superpose the gaze direction onto the visual observation field.

13. The device as recited in claim 9, wherein the sensor unit is further designed to adjust at least one of a resolution and accuracy of the estimated visual observation field based on at least one of a number and a position of the at least one optical feature.

* * * * *